United States Patent
Levi et al.

(10) Patent No.: US 11,253,490 B1
(45) Date of Patent: Feb. 22, 2022

(54) COMPOSITIONS AND METHODS OF TREATING COGNITIVE IMPAIRMENT

(71) Applicant: Vallon Pharmaceuticals, Inc., Philadelphia, PA (US)

(72) Inventors: Ofir Levi, Tel Aviv (IL); David Baker, Philadelphia, PA (US); Timothy Whitaker, Bryn Mawr, PA (US)

(73) Assignee: Vallon Pharamaceuticals, Inc., Philadelphia, PA (US)

( * ) Notice: Subject to any disclaimer, the term of this patent is extended or adjusted under 35 U.S.C. 154(b) by 0 days.

(21) Appl. No.: 17/322,316

(22) Filed: May 17, 2021

(51) Int. Cl.
| | | |
|---|---|---|
| *A61K 31/137* | (2006.01) | |
| *A61K 9/48* | (2006.01) | |
| *A61K 47/32* | (2006.01) | |
| *A61K 47/14* | (2017.01) | |
| *A61K 47/36* | (2006.01) | |

(52) U.S. Cl.
CPC .......... *A61K 31/137* (2013.01); *A61K 9/4808* (2013.01); *A61K 47/14* (2013.01); *A61K 47/32* (2013.01); *A61K 47/36* (2013.01)

(58) Field of Classification Search
CPC .... A61K 31/137; A61K 9/4808; A61K 47/14; A61K 47/32; A61K 47/36
See application file for complete search history.

(56) References Cited

U.S. PATENT DOCUMENTS 9,931,303 B1 * 4/2018 Daniely .............. A61K 9/4866

OTHER PUBLICATIONS

Jaywant et al., Neuropsychopharmacology, 2021,0:1-6; published: Jan. 20, 21. (Year: 2021).*
Belluck, P., "'I Feel Like I Have Dementia': Brain Fog Plagues Covid Survivors," The New York Times, Oct. 11, 2020, 7 pages.
George, J., "Most Hospitalized COVID Patients Have Neurologic Symptoms—Severe complications seen in all stages of COVID-19, including recovery," MedPage Today, Jun. 5, 2020, 3 pages.
Heneka et al., "Immediate and long-term consequences of COVID-19 infections for the development of neurological disease," Alzheimer's Research & Therapy (2020) 12:69, 3 pages.
Jaywant et al., "Frequency and profile of objective cognitive deficits in hospitalized patients recovering from COVID-19," Neuropsychopharmacology (2021) 0:1-6; https://doi.org/10.1038/s41386-021-00978-8.
Ritchie et al., "The cognitive consequences of the COVID-19 epidemic: collateral damage?" Brain Communications 2020: 5 pages, doi:10.1093/braincomms/fcaa069.
Zhou et al., "The landscape of cognitive function in recovered COVID-19 patients," Journal of Psychiatric Research 129 (2020) 98-102.

* cited by examiner

*Primary Examiner* — Genevieve S Alley
(74) *Attorney, Agent, or Firm* — Cooley LLP; Cynthia A. Kozakiewicz

(57) ABSTRACT

The present invention relates generally method of treating or alleviating cognitive impairment by administering an abuse-deterrent formulation containing dextroamphetamine sulfate.

7 Claims, No Drawings

COMPOSITIONS AND METHODS OF TREATING COGNITIVE IMPAIRMENT

FIELD OF THE INVENTION

The present invention relates generally treating or alleviating a symptom of cognitive impairment with an abuse deterrent formulation of dextroamphetamine, or a pharmaceutically acceptable salt thereof. More specifically, cognitive impairment associated with COVID-19.

BACKGROUND OF THE INVENTION

Cognitive impairment can an prevent an individual from concentrating, recalling memories, and can lead to mental fatigue.

Cognitive impairment is not caused by any one disease or condition, nor is it limited to a specific age group. Cognitive impairment, effects one's quality of life and is complicated to treat because it can be caused by a long range of lifestyle problems, medications, or conditions.

However, new research is now suggesting that there may be long-term neurologic consequences in those who survive COVID infections, including more than seven million Americans and another 27 million people worldwide. Particularly troubling is increasing evidence that there may be mild—but very real—brain damage that occurs in many survivors, causing pervasive yet subtle cognitive, behavioral, and psychological problems. While sometimes the brain damage is obvious and leads to major cognitive impairment, more frequently the damage is mild, leading to difficulties with sustained attention.

Accordingly, a need exists for treatments for cognitive impairment, in particular in COVID 19 survivors.

SUMMARY OF THE INVENTION

The disclosure provides method of treating or alleviating a symptom of cognitive impairment comprising administering to a subject whom has had a COVID-19 infection an abuse-deterrent formulation of dextroamphetamine or a pharmaceutically acceptable salt thereof, a poloxamer 124, a gellan gum, and a polyoxyl stearate. The ratio of poloxamer 124:gellan gum:polyoxyl stearate is about 40:30:30.

The poloxamer 124 is Kollisolv™ P124, the gellan gum Kelcogel™ CGHA, and the polyoxyl stearate is Gelucire™ 48/16. The dextroamphetamine is at a unit dose of about 10 mg to about 50 mg.
The formulation is administered once a day. The formulation is in the form of a capsule, for example a hard shell capsule.

Symptoms of cognitive impairment include for example, problems in concentration in studies and/or work; exhibiting reluctance or difficulty in acquiring new skills; finding multitasking jobs daunting; confusion; short-term memory loss; not able to give attention to a particular thing for a long time; slow in completing usual tasks; difficulty in recalling a conversation or finding the right word to form a sentence; forgetfulness with image or list of words; fatigue, mild depression, or anxiety.

In some aspects, the subject has received mechanical ventilation.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

The invention provides composition and methods of treating or alleviating a symptom of cognitive impairment. Cognitive impairment is a is state of diminished mental capacity marked by an inability to concentrate, think or reason clearly.

Cognitive impairment can be mild to severe and can affect performance on virtually any cognitive task. Cognition includes perception, memory, learning, executive functions, language, constructive abilities, voluntary motor control, attention, and mental speed. The extent of the impairment is variable because inattention may impair several cognitive functions.

Cognitive impairment can be caused by an underlying acute or chronic disease or disorder. Conditions that can cognitive impairment, include, stress, anxiety, depression, lack of sleep, hormonal changes (e.g. menopause, perimenopause, pregnancy, birth control medications), medications (e.g., chemotherapy, oxybutynin, diphenhydramine, amitriptyline); underactive thyroid, nutritional deficiency (e.g., low levels of Vitamin B12), food intolerance, allergy, chronic infection (e.g., candidiasis), multiple sclerosis, chronic fatigue syndrome, fibromyalgia, mechanical ventilation and metal poisoning (e.g., mercury, cadmium, lead). More recently, patients recovering from COVID-19 report experiencing neurological symptoms, including cognitive impairment, which can reflect a wide variety of neurological and psychological symptoms linked to COVID-19.

Often, cognitive impairment can be treated by treating the underlining condition, such as treating the underactive thyroid with thyroid hormone. However, cognitive impairment caused by chemotherapy, mechanical ventilation and Covid-19 have few if any treatment options.

Dextroamphetamine, has been demonstrated to improve cognitive measures in patients with ADHD, menopause and executive cogitative impairment. Given, the large number of potential individuals whom dextroamphetamine could be useful in treating or alleviating symptoms of brain fog, an abuse deterrent formulation would be preferred to avoid misuse and abuse. Abuse deterrent formulations of amphetamine and dextroamphetamine are known in the art, such as ADAIR (Abuse-Deterrent Amphetamine Immediate-Release) See. WO, the contents of which are incorporated by reference in its entirety According, the present disclosure provides methods of treating or alleviating a symptom of cognitive impairment in a subject by administering an immediate release abuse deterrent formulation containing amphetamines such as dextroamphetamine or a pharmaceutically acceptable salt thereof. Preferably the abuse deterrent formulation is ADAIR.

Common signs and symptoms cognitive impairment include for example, problems in concentration in studies and/or work; exhibiting reluctance or difficulty in acquiring new skills; finding multitasking jobs daunting; confusion; short-term memory loss; not able to give attention to a particular thing for a long time; slow in completing usual tasks; difficulty in recalling a conversation or finding the right word to form a sentence; forgetfulness with image or list of words; fatigue, mild depression, and anxiety. Cognitive impairment can be measured by methods known in the art, such as for example, the Cambridge Neuropsychological Test Automated Battery (CANTAB)), or the Hopkins Verbal Learning Test Revised. The subject is a pediatric subject. Alternatively, the subject is an adult. The subject has received chemotherapy. The subject has had Covid-19 or received mechanical ventilation.

The unit dose of dextroamphetamine is between about 10-50 mg. For example, the unit dose is 5 mg, 10 mg, 15 mg, 20 mg, 25 mg, 30 mg, 35 mg, 40 mg, 45 mg, or 50 mg. The unit does is administered once, twice, three, or four times daily. The daily does is between 5 mg and 100 mg. For example the daily dose is 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95, mg or 100 mg.

The formulation contains one or more excipients. The excipients are selected to prevent abuse of dextroamphetamine.

Suitable abuse deterrent excipients may display one or more of the following properties. high melting point excipients resistant to heating and that prevent injecting; taste modifiers which prevent covert administration, snorting and dose dumping; water insolubles that are resistant to extraction and that prevent drink adulteration; waxy excipients that prevent snorting; viscosity modifiers resistant to dissolution and that prevent injecting and dose dumping; low density excipients that prevent drink adulteration; and dyes that disclose abuse of the pharmaceutical medicament.

Exemplary excipients include for example thermosoftening pharmaceutical bases including waxes, poloxamers, macrogol glycerides, PEGs, glycerol monooleates or monostearates, PEG esters such as polyoxyl stearate, hydrogenated or partially hydrogenated glycerides and hard fats such as beeswax, poloxamer 188, poloxamer 124, Gelucires™ polyethylene 6000, glycerol monostearate, hydrogenated palm kernel oil, hydrogenated cottonseed oil, Softisan™ 138, Gelucire™ 40/01, hexadecan-1-ol; Thixotropes such as fumed silica and pulverised attapulgite and viscosity modifiers such as hydroxyl propyl methyl cellulose or Gellan gum to increase viscosity or the standard pharmaceutical or food grade oils such as fractionated coconut oil, soybean oil etc. to decrease viscosity.

Preferably, the abuse deterrent excipients include a poloxamer, a water-soluble anionic polysaccharide and a PEG ester. Preferably, the poloxamer is poloxamer 124 such as Kollisolv™. Preferably, the water soluble anionic polysaccharide is gellan gum such as Kecogel CGHA™. Preferably, the PEG ester is polyoxyl stearate such as Gelucire 48/16™.

The abuse deterrent formulation of dextroamphetamine may be in a capsule form, such as a hard shell liquid filled capsule. For example, the capsule comprises gelatin. Alternatively, the capsule comprises hydroxypropyl methylcellulose (HPMC), pullulan or other hard shell material.

An important aspect of the invention is that the dextroamphetamine of the abuse deterrent formulation performs normally when taken as intended. For example, the abuse deterrent dextroamphetamine formulation is orally bioavailable and has a dissolution profile similar to the profile of a non-abuse deterrent formulation of dextroamphetamine. In some embodiments, the abuse-abuse deterrent formulation has a dissolution profile wherein release of the dextroamphetamine in solution is complete within 45 minutes.

The abuse-deterrent formulation of dextroamphetamine useful in the method of the disclosure comprise at least two excipients selected from PEG ester, poloxamer, water-soluble anionic polysaccharide, and carboxymethylcellulose.

In some embodiments, the abuse-deterrent formulation of dextroamphetamine comprises at least two excipients selected from Kollisolv™ P124, Kolliphor™ EL, Kolliphor™ RH40, Tween™ 20, Gelucire™ 48/16, Gelucire™ 44/14, Super refined Corn Oil, Aerosil™ 200, Luxura™, Xantural™ 75, Kelcogel™ CGHA, CMC 7H3SF, Methocel™ A4CP, Gelatin Type B 220 Bloom, and PEG6000.

In some embodiments, the abuse-deterrent formulation of dextroamphetamine comprises a medicament, PEG ester, poloxamer, and water-soluble anionic polysaccharide. In specific embodiments, the PEG ester is polyoxyl stearate; the poloxamer is poloxamer 124; and the water-soluble anionic polysaccharide is gellan gum. In some embodiments, the ratio of poloxamer:polysaccharide:PEG ester is about 40:30:30.

In some embodiments, the abuse-deterrent formulation of dextroamphetamine comprises medicament, PEG ester, and water-soluble anionic polysaccharide. In specific embodiments, the PEG ester is polyoxyl stearate; and the water-soluble anionic polysaccharide is gellan gum. In further specific embodiments, the ratio of PEG ester:water-soluble anionic polysaccharide is about 70:30.

In yet another embodiment, the abuse-deterrent formulation comprises medicament, PEG ester, and carboxymethylcellulose. In specific embodiments, the PEG ester is polyoxyl stearate. In further specific embodiments, the ratio of PEG ester and carboxymethylcellulose is about 70:30.

In some embodiments, the abuse-deterrent formulation comprises a medicament, Kollisolv™ P124, Kelcogel™ CGHA, and Gelucire™ 48/16. In further specific embodiments, the ratio of Kollisolv™ P124, Kelcogel™ CGHA, and Gelucire™ 48/16 is about 40:30:30.

In some embodiments, the abuse-deterrent formulation comprises a medicament, Gelucire™ 48/16 and Kelcogel™ CGHA. In further specific embodiments, the ratio of Gelucire™ 48/16 and Kelcogel™ CGHA is about 70:30.

In some embodiments, the abuse-deterrent formulation comprises a medicament, Kolliphor™ EL and CMC 7H3SF. In further specific embodiments, the ratio of Kolliphor™ EL and CMC 7H3SF is about 70:30.

The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of +/−5%, or +/−10%.

"Amphetamine" as used herein has the formula:

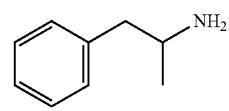

"Dextroamphetamine" as used herein is the S enantiomer of amphetamine and has the formula:

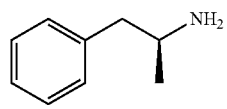

In some embodiments, the abuse-deterrent formulation comprises one or more medicaments is dextroamphetamine saccharate or dextroamphetamine sulfate.

In preferred embodiments the abuse-deterrent formulation of dextroamphetamine, a poloxamer, a water-soluble anionic polysaccharide, and a PEG ester.

The poloxamer is poloxamer 124. The water-soluble anionic polysaccharide is gellan gum. The PEG ester is polyoxyl stearate. The ratio of poloxamer:water-soluble anionic polysaccharide:PEG ester is about 40:30:30. The abuse-deterrent formulation included 33-43 wt % of poloxamer; 24-32 wt % of water-soluble anionic polysaccharide; and 24-32 wt % of PEG ester. The ratio of poloxamer 124:gellan gum:polyoxyl stearate is about 40:30:30. The poloxamer is Kollisolv™ P124, the water-soluble anionic polysaccharide is Kelcogel™ CGHA, and the PEG ester is Gelucire™ 48/16.

A preferred formulation includes dextroamphetamine, or a pharmaceutically acceptable salt as thereof poloxamer 124, gellan gum, and polyoxyl stearate where the ratio of poloxamer 124:gellan gum:polyoxyl stearate is about 40:30:30. In some embodiments, the poloxamer 124 is Kollisolv™ P124, the gellan gum is Kelcogel™ CGHA, and the polyoxyl stearate is Gelucire™ 48/16.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating or alleviating a symptom of cognitive impairment comprising administering to a subject whom has had a COVID-19 infection an abuse-deterrent formulation comprising a unit dose of about 10 mg to about 50 mg dextroamphetamine or a pharmaceutically acceptable salt thereof, poloxamer 124, gellan gum, and polyoxyl stearate.

2. The method of claim 1, wherein the ratio of poloxamer 124:gellan gum:polyoxyl stearate is about 40:30:30.

3. The method of claim 1, wherein the formulation is administered once a day.

4. The method of claim 1, wherein the formulation is in the form of a capsule.

5. The method of claim 4, wherein the capsule is a hard shell capsule.

6. The method of claim 1, wherein the symptom of cognitive impairment is problems in concentration in studies and/or work; exhibiting reluctance or difficulty in acquiring new skills; finding multitasking jobs daunting; confusion; short-term memory loss; not able to give attention to a particular thing for a long time; slow in completing usual tasks; difficulty in recalling a conversation or finding the right word to form a sentence; forgetfulness with image or list of words; fatigue, mild depression, or anxiety.

7. The method of claim 1, wherein the subject has received mechanical ventilation.

* * * * *